United States Patent [19]

Miesel

[11] 4,219,557
[45] Aug. 26, 1980

[54] 1-(2,6-DIHALOBENZOYL)-3-(5-SUBSTITUTED-2-PYRIDINYL)UREA COMPOUNDS AND INSECTICIDAL USE

[75] Inventor: John L. Miesel, Indianapolis, Ind.

[73] Assignee: Eli Lilly and Company, Indianapolis, Ind.

[21] Appl. No.: 938,723

[22] Filed: Aug. 31, 1978

[51] Int. Cl.$^2$ ...................... A01N 9/22; C07D 213/75
[52] U.S. Cl. ...................................... 424/263; 546/306
[58] Field of Search ......................... 546/306; 424/263

[56] References Cited

U.S. PATENT DOCUMENTS

| | | | |
|---|---|---|---|
| 3,748,356 | 7/1973 | Wellinga et al. | 546/306 X |
| 4,083,977 | 4/1978 | Miesel | 424/250 |
| 4,092,421 | 5/1978 | Wade et al. | 424/266 |

OTHER PUBLICATIONS

DeMilo et al, J. Agr. & Food Chem., vol. 26, No. 1 (Jan./Feb. 1978) pp. 164–166.
Abstract of Papers of 174th meeting of ACS (Port City Press, Inc., Baltimore, Md.), undated.
C & E News, Jul. 25, 1977, pp. 24 and 57.
Wellinga et al, J. Agr. & Food Chem., vol. 21, No. 3 (1973) pp. 348–354.
Wellinga et al, J. Agr. & Food Chem., vol. 21, No. 6 (1973) pp. 993–998.
Hajjar et al, Science, vol. 200 (1978) pp. 1499–1500.

*Primary Examiner*—Richard Raymond
*Attorney, Agent, or Firm*—Kathleen R. S. Page; Arthur R. Whale

[57] ABSTRACT

The present invention is directed to 1-(2,6-dihalobenzoyl)-3-(5-substituted-2-pyridinyl)urea compounds useful as insecticides.

12 Claims, No Drawings

1-(2,6-DIHALOBENZOYL)-3-(5-SUBSTITUTED-2-PYRIDINYL)UREA COMPOUNDS AND INSECTICIDAL USE

SUMMARY OF THE INVENTION

More particularly, the present invention is directed to novel compounds of the formula

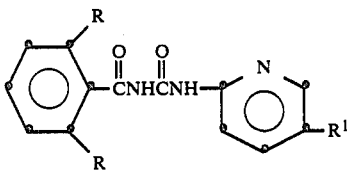

wherein R is in both occurrences the same moiety and is either chloro or fluoro; and $R^1$ is chloro, bromo, or trifluoromethyl; and the acid addition salts thereof and the N-oxides of those compounds wherein $R^1$ is bromo or trifluoromethyl.

The present invention is also directed to methods employing and compositions comprising the above compounds as insecticides.

DETAILED DESCRIPTION OF THE INVENTION

For the purposes of the present application, the compounds of this invention are named substituted ureas, with numbering as follows:

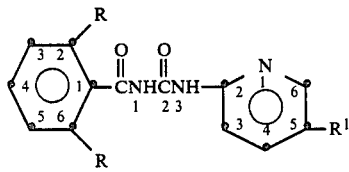

Thus, the compounds are named as 1-(2,6-dihalobenzoyl)-3-(5-$R^1$-2-pyridinyl)ureas, or N-oxides thereof, or acid addition salts thereof.

The compounds of the present invention are readily prepared by the reaction of a 2,6-dihalobenzoyl isocyanate of the formula

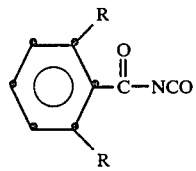

with a 2-aminopyridine of the formula

or an N-oxide thereof. The reaction is preferably conducted in an organic solvent such as ethyl acetate, dichloroethane, methylene chloride, or the like, and at room temperatures or slightly elevated temperatures such as up to 50° C. The reaction consumes the reactants in equimolar amounts.

The acid addition salts are prepared by reacting a product, derived by reaction with a 2-aminopyridine, with the desired acid, in conventional procedures. Acids having a pKa of 3 or lower are preferred, and generally the mineral acids are preferred.

The 2,6-dihalobenzoyl isocyanates to be employed as starting materials are readily prepared from the corresponding 2,6-dihalobenzamides, which are commercially available, by the method of Speziale et al., *J. Org. Chem.* 27, 3742 (1962); and Wellinga et al., *J. Agric. Food Chem.* 21, 348 and 993 (1973). In this method, the benzamide is reacted with oxalyl chloride. An improved method for carrying out this reaction is illustrated in Example 5, below.

The 5-bromo- and 5-chloro-2-aminopyridine starting materials are commercially available. The 5-(trifluoromethyl)-2-aminopyridine is prepared by the method of U.S. Pat. No. 3,681,369. The N-oxides thereof are prepared by the method of Deady, *Synthetic Communications* 7(8), 509–514 (1977). The resulting 2-aminopyridine N-oxide is then reacted with a 2,6-dihalobenzoyl isocyanate in accordance with the general procedure, above, to obtain the N-oxide of the final product.

The following examples illustrate the synthesis of the compounds of the present invention.

EXAMPLE 1: 1-(2,6-DICHLOROBENZOYL)-3-(5-CHLORO-2-PYRIDINYL)-UREA 2,6-Dichlorobenzoyl isocyanate (2.2 grams; 0.01 mole) and 5-chloro-2-aminopyridine (1.3 grams; 0.01 mole) were mixed in about 50 ml. of ethyl acetate, at room temperature, and the reaction mixture was stirred overnight (about 18 hours) at room temperature. Solvent was then evaporated, water was added, and the product was extracted with ethyl acetate. The ethyl acetate was evaporated, and the product recrystallized from ethanol, m.p., 211°–215° C. Elemental analysis showed the following:
Calculated: C, 45.31; H, 2.34; N, 12.19. Found: C, 45.12; H, 2.64; N, 12.36.

EXAMPLE 2: 1-(2,6-DICHLOROBENZOYL)-3-(5-BROMO-2-PYRIDINYL)-UREA 2,6-Dichlorobenzoyl isocyanate (2.16 grams; 0.01 mole) and 5-bromo-2-aminopyridine (1.73 grams; 0.01 mole) were mixed in 50 ml. of ethyl acetate, at room temperature. The reaction mixture was stirred at room temperature for 4 hours, during which the product precipitated. It was separated by filtration and recrystallized from ethanol, m.p. 228°–230° C., yield 2.0 grams. Elemental analysis showed:
Calculated: C, 40.14; H, 2.07; N, 10.80. Found: C, 39.95; H, 1.94; N, 10.60.

EXAMPLE 3: 1-(2,6-DICHLOROBENZOYL)-3-(5-(TRIFLUOROMETHYL)-2-PYRIDINYL)UREA 2,6-Dichlorobenzoyl isocyanate (1.1 grams; 0.005 mole) and 5-(trifluoromethyl)-2-aminopyridine (800 mg; 0.005 mole) were mixed in 50 ml. of ethyl acetate at room temperature and stirred overnight (about 18 hours) at room temperature. Solvent was then evaporated and the product recrystallized from ethanol, m.p. 228°–230° C., yield 200 mg. Elemental analysis showed:

Calculated: C, 44.47; H, 2.13; N, 11.11. Found: C, 44.42; H, 2.19; N, 11.18.

EXAMPLE 4:
1-(2,6-DICHLOROBENZOYL)-3-(5-CHLORO-2-PYRIDINYL)-UREA

5-Chloro-2-aminopyridine (450 grams; 3.5 moles) and 5000 ml. of 1,2-dichloroethane were slurried together. The flask was then purged with nitrogen and a cold water bath applied, resulting in a lowering of the temperature to 20° C. 2,6-Dichlorobenzoyl isocyanate (912 grams; 4.2 moles) was added dropwise over one hour, holding the temperature at <30° C. The reaction mixture was stirred for 10 minutes, the cold water bath was removed, and a hot tap water bath (about 55° C.) was applied. The flask temperature rose to 42° C. and was held at 40° C. for 30 minutes. TLC showed that all starting material had been reacted. Solvent was removed on a rotary evaporator, and the solid residue was slurried with 1 liter of methanol, chilled and filtered. Yield was 1177 grams. m.p. 219°–222° C. Identity of the product was confirmed by NMR and IR.

EXAMPLE 5:
2,6-DICHLOROBENZOYL ISOCYANATE

A one-liter flask was purged with nitrogen while dry 2,6-dichlorobenzamide (125 grams; 0.64 mole) and dry toluene (300 ml.) were added. The nitrogen purge was continued as oxalyl chloride (100 grams; 0.79 mole) was added over a 15-minute period, at room temperature and with stirring. The reaction mixture was heated to 55° C. and stirred overnight (about 18 hours) at 55° C.

The reaction mixture was then heated to reflux (111° C.) and refluxed for 2 hours. Solvent was removed under vacuum and the product distilled off at 134°–135° C. flask temperature and 131°–132° C. vapor temperature, at 13 mm. vacuum, yield 127.5 grams (92.5%).

EXAMPLE 6:
1-(2,6-DICHLOROBENZOYL)-3-(5-BROMO-2-PYRIDINYL)-UREA N-OXIDE

5-Bromo-2-aminopyridine N-oxide (0.37 gram) was partially dissolved in 25 ml. of acetonitrile and 2,6-dichlorobenzoyl isocyanate (0.5 gram) was added under nitrogen and at room temperature. The reaction mixture was stirred overnight (about 18 hours) and the product precipitated. It was separated by filtration, yield 280 mg., m.p. 230°–235° C.

Calculated: C, 38.55; H, 1.99; N, 10.37. Found: C, 38.82; H, 1.98; N, 10.62.

EXAMPLES 7–11

Other representative compounds of the present invention include the following:

EXAMPLE 7

1-(2,6-difluorobenzoyl)-3-(5-chloro-2-pyridinyl)urea, m.p., 226°–229° C.

Calculated: C, 50.10; H, 2.59; N, 13.48. Found: C, 49.88; H, 2.51; N, 13.21.

EXAMPLE 8

1-(2,6-difluorobenzoyl)-3-(5-bromo-2-pyridinyl)urea.

EXAMPLE 9

1-(2,6-difluorobenzoyl)-3-(5-trifluoromethyl)-2-pyridinyl)urea, m.p., 215°–220° C.

Calculated: C, 48.71; H, 2.34; N, 12.17. Found: C, 48.90; H, 2.39; N, 12.37.

EXAMPLE 10

1-(2,6-difluorobenzoyl)-3-(5-chloro-2-pyridinyl)-urea, hydrobromide.

EXAMPLE 11

1-(2,6-dichlorobenzoyl)-3-(5-chloro-2-pyridinyl)-urea, hydrochloride.

The compounds of the present invention are useful for the control of insects of various orders, including Coleoptera such as Mexican bean beetle, boll weevil, corn rootworms, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, white grubs; Diptera, such as house fly, yellow fever mosquito, stable fly, horn fly, blowfly, cabbage maggot, carrot rust fly; Lepidoptera, such as southern armyworm, codling moth, cutworm, clothes moth, Indian meal moth, leaf rollers, corn earworm, European corn borer, cabbage worm, cabbage looper, cotton bollworm, bagworm, eastern tent caterpillar, sod webworm, fall armyworm; and Orthoptera, such as German cockroach and American cockroach.

It is believed that the present compounds act by interfering with the mechanism of metamorphosis which occurs in insects, causing the death of the insects. It is also believed that ingestion by the insects is necessary to invoke this mechanism. While the death of any given insect may be delayed until that insect reaches some stage of metamorphosis, the net result of this activity is the control and suppression of insects.

Therefore, in another embodiment, the present invention is directed to a method of suppressing insects which comprises applying to a locus of the insects an effective amount of a compound of the present invention. The locus can be any environment inhabited by insects to be controlled, such as soil, air, water, foods, vegetation, manure, inert objects, stored matter such as grain, and the like.

Preferably the compounds of the present invention are supplied in a formulation, for ease of application. The compounds can be formulated with various adjuvants, including water, organic liquids, surface-active agents, inert solids, and the like. Suitable surface-active agents include anionic agents, such as sodium lauryl sulfate, sodium dodecylbenzenesulfonate, and the like; and nonionic agents, such as polyethylene glycol p-nonylphenyl ether. Mixtures are often desirably employed. The formulation can take the form of a liquid, dust, granule, aerosol, etc. The formulation can be concentrated, as in a slow-release formulation or as in a formulation to be diluted with water before application to the locus of insects. Many methods of formulation are known in the art and can be employed in implementing the present invention.

The concentration of active agent in the formulation is not critical, inasmuch as an effective concentration will vary with the nature of the locus to be treated, the severity of insect infestation, the susceptibility of the particular insects involved, etc. In general, concentrations ranging from about 0.1 to 1000 ppm give good results. As exemplified by Table 3, below, lesser concentrations of from about 5 to about 100 ppm have given good control of southern armyworm.

The insecticidal activity of the present compounds was determined by testing the efficacy of formulations of the compounds against Mexican bean beetle larvae (*Epilachna varivestis*), and against southern armyworm larvae (*Spodoptera eridania*). These insects are members of the Coleoptera and Lepidoptera orders of insects, respectively. The formulations were applied to the foliage of plants and the larvae were subsequently permitted to feed on the foliage. The compounds were tested in a plurality of concentrations, from a concentration of about 1000 ppm. to about 1 ppm.

Each compound to be tested was formulated by dissolving 10 mg. of the compound in 1 ml. of a solvent made up with 23 grams of Toximul R and 13 grams of Toximul S per liter of 1:1 anhydrous ethanol and acetone. Each of Toximul R and Toximul S is a sulfonate/nonionic blend produced by Stepan Chemical Company, Northfield, Illinois. Water was then added to obtain 10 ml. of solution containing the compound in a concentration of 1000 parts per million. Alternatively, 11 mg. of compound was used, to make up 11 ml. of solution, of which 10 ml. was employed as a 1000 ppm. treating solution, and of which the remaining 1 ml. was diluted further with water to obtain a treating solution containing 100 ppm of compound. Formulations of the compound at lesser concentrations were prepared in the same manner, using the same solvent.

Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×20 mm. plastic petri dishes. Five second-instar Mexican bean beetle larvae (*Epilachna varivestis*) and five second- and third-instar southern armyworm larvae (*Spodoptera eridania*) were placed in each of three dishes. The dishes were then placed in a room wherein the temperature and relative humidity were controlled at about 78° F. and about 51 percent, respectively, for a period of four days, at which time the first evaluation of the effects of the test compounds was made. After this evaluation, two fresh leaves from the original treated pots were placed in each dish. The dishes were again maintained in the temperature and humidity controlled room for an additional three days until the final seven-day evaluation was made.

Insecticidal effect was determined by counting the number of living larvae of each species and applying the following rating code:
0=all larvae living
1=half or more than half of the larvae living
2=less than half of the larvae living
3=all larvae dead The results of this test are set forth in Table 1, which follows. In the table, column 1 identifies the compounds by the number of the preparative example; column 2 lists the concentration of the test compound in the formulation; and columns 3 through 6 give the rating code at days 4 and 7 for the two insects against which the compounds were tested.

Table 1

| Example | Appln. Rate ppm | Insect Control Mexican Bean Beetle 4 days | 7 days | Southern Armyworm 4 days | 7 days |
|---|---|---|---|---|---|
| 1 | 1000 | 1 | 2 | 3 | 3 |
| 2 | 1000 | 0 | 3 | 3 | 3 |
| 2 | 100 | 0 | 2 | 3 | 3 |

Table 1-continued

| Example | Appln. Rate ppm | Insect Control Mexican Bean Beetle 4 days | 7 days | Southern Armyworm 4 days | 7 days |
|---|---|---|---|---|---|
| 3 | 1000 | 2 | 2 | 3 | 3 |
| 6 | 1000 | 2 | 2 | 3 | 3 |
| 6 | 100 | 0 | 1 | 2 | 3 |
| 7 | 1000 | 2 | 3 | 2 | 3 |
| 7 | 100 | 1 | 3 | 1 | 2 |
| 9 | 1000 | 3 | 3 | 3 | 3 |
| 9 | 100 | 3 | 3 | 2 | 2 |

In a further evaluation, the compounds of the present invention were retested in the same procedure described above but at lower concentrations. In the retest, percent control was determined by counting the number of living larvae per dish and using Abbott's formula [W. W. Abbott, "A Method of Computing the Effectiveness of an Insecticide", *J. Econ. Entomol.* 18, 265-7 (1925)]:

$$\text{Percent Control} = \frac{\text{No. of survivors in control} - \text{No. of survivors in treatment} \times 100}{\text{No. survivors in control}}$$

The results are set forth in Tables 2 and 3 which follow.

Table 2

| Example No. | Appln. Rate ppm | Percent Control of Mexican Bean Beetle 4 days | 7 days |
|---|---|---|---|
| 1 | 10 | 26 | 26 |
|   | 25 | 19 | 10 |
|   | 50 | 19 | 21 |
|   | 100 | 7 | 42 |
| 3 | 25 | 26 | 73 |
|   | 50 | 80 | 93 |
|   | 100 | 73 | 73 |
| 3 | 2.5 | 0 | 20 |
|   | 5 | 6 | 66 |
|   | 10 | 33 | 93 |
|   | 20 | 26 | 73 |

Table 3

| Example No. | Appln. Rate ppm | Percent Control of Southern Armyworm 4 days | 7 days |
|---|---|---|---|
| 1 | 1.0 | 0 | 7 |
|   | 2.5 | 13 | 93 |
|   | 5 | 33 | 93 |
|   | 10 | 67 | 100 |
|   | 100 | 93 | 100 |
| 2 | 10 | 93 | 100 |
|   | 25 | 93 | 100 |
|   | 50 | 100 | 100 |
|   | 100 | 100 | 100 |
| 2 | 1.0 | 0 | 20 |
|   | 2.5 | 47 | 93 |
|   | 5 | 86 | 100 |
|   | 10 | 100 | 100 |
| 3 | 25 | 100 | 100 |
|   | 50 | 100 | 100 |
|   | 100 | 100 | 100 |
| 3 | 2.5 | 66 | 86 |
|   | 5. | 100 | 100 |
|   | 10. | 100 | 100 |
|   | 20 | 100 | 100 |

I claim:
1. Compound of the formula

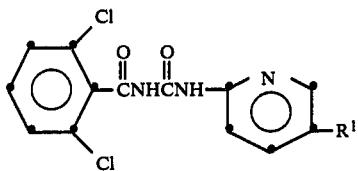

wherein R¹ is chloro, bromo, or trifluoromethyl; or an acid addition salt thereof or an N-oxide of a compound wherein R¹ is bromo or trifluoromethyl.

2. The compound of claim 1 which is 1-(2,6-dichlorobenzoyl)-3-(5-chloro-2-pyridinyl)urea or an acid addition salt thereof.

3. The compound of claim 1 which is 1-(2,6-dichlorobenzoyl)-3-(5-bromo-2-pyridinyl)urea or an acid addition salt thereof.

4. The compound of claim 1 which is 1-(2,6-dichlorobenzoyl)-3-(5-(trifluoromethyl)-2-pyridinyl)urea or an acid addition salt thereof.

5. Composition comprising a surface active agent and an insecticidally effective amount of an active agent which is a compound of claim 1.

6. The composition of claim 5 wherein the active agent is 1-(2,6-dichlorobenzoyl)-3-(5-chloro-2-pyridinyl)urea or an acid addition salt thereof.

7. The composition of claim 5 wherein the active agent is 1-(2,6-dichlorobenzoyl)-3-(5-bromo-2-pyridinyl)urea or an acid addition salt thereof.

8. The composition of claim 5 wherein the active agent is 1-(2,6-dichlorobenzoyl)-3-(5-(trifluoromethyl)-2-pyridinyl)urea or an acid addition salt thereof.

9. Method of suppressing insects of an order selected from the group consisting of Coleoptera, Diptera, Lepidoptera, and Orthoptera, which comprises applying to a locus of the insects an effective amount of an active agent which is a compound of claim 1.

10. The method of claim 9 wherein the active agent is 1-(2,6-dichlorobenzoyl)-3-(5-chloro-2-pyridinyl)urea or an acid addition salt thereof.

11. The method of claim 9 wherein the active agent is 1-(2,6-dichlorobenzoyl)-3-(5-bromo-2-pyridinyl)urea or an acid addition salt thereof.

12. The method of claim 9 wherein the active agent is 1-(2,6-dichlorobenzoyl)-3-(5-(trifluoromethyl)-2-pyridinyl)-urea or an acid addition salt thereof.

* * * * *